United States Patent
Cezario et al.

(10) Patent No.: US 10,351,757 B2
(45) Date of Patent: Jul. 16, 2019

(54) COMPOSITION FOR REMOVING ORGANIC DEPOSITS FROM OIL AND GAS WELLS AND OTHER SUBSURFACE SYSTEMS AND METHOD FOR REMOVING ORGANIC DEPOSITS USING THE REMOVER COMPOSITION

(71) Applicants: PETRÓLEO BRASILEIRO S.A.-PETROBRAS, Rio de Janeiro (BR); Wendel Rodrigues Cezario, Itaboraí (BR); Rodrigo Pio Borges Menezes, Rio de Janeiro (BR); Pedro Aledi Portugal, Rio de Janeiro (BR); Rosana Serfaty De Campos, Rio de Janeiro (BR); Guilherme dos Santos Vieira Lima, Niterói (BR); Plinio Martins Dias Da Silva, Rio de Janeiro (BR)

(72) Inventors: Wendel Rodrigues Cezario, Itaboraí (BR); Rodrigo Pio Borges Menezes, Rio de Janeiro (BR); Pedro Aledi Portugal, Rio de Janeiro (BR); Rosana Serfaty De Campos, Rio de Janeiro (BR); Guilherme dos Santos Vieira Lima, Niterói (BR); Plinio Martins Dias Da Silva, Rio de Janeiro (BR)

(73) Assignee: PETRÓLEO BRASILEIRO S.A.-PETROBRAS, Rio de Janeiro (BR)

( * ) Notice: Subject to any disclaimer, the term of this patent is extended or adjusted under 35 U.S.C. 154(b) by 0 days.

(21) Appl. No.: 15/538,916

(22) PCT Filed: Jun. 12, 2015

(86) PCT No.: PCT/BR2015/000085
§ 371 (c)(1),
(2) Date: Jun. 22, 2017

(87) PCT Pub. No.: WO2017/000049
PCT Pub. Date: Jan. 5, 2017

(65) Prior Publication Data
US 2018/0086967 A1    Mar. 29, 2018

(51) Int. Cl.
C07C 15/085 (2006.01)
C09K 8/524 (2006.01)
E21B 37/06 (2006.01)

(52) U.S. Cl.
CPC ............ C09K 8/524 (2013.01); C07C 15/085 (2013.01); E21B 37/06 (2013.01); *C10L 2200/0476* (2013.01)

(58) Field of Classification Search
USPC ........................................ 507/131, 242, 244
See application file for complete search history.

(56) References Cited

U.S. PATENT DOCUMENTS

| 2,753,939 | A | 7/1956 | Carpenter et al. |
| 4,090,562 | A | 5/1978 | Maly et al. |
| 4,925,497 | A | 5/1990 | Thierheimer, Jr. |
| 2003/0045605 | A1 | 3/2003 | Thompson |
| 2006/0142172 | A1 | 6/2006 | Cioletti et al. |
| 2013/0079255 | A1* | 3/2013 | Del Gaudio ........... C09K 8/524 507/90 |

FOREIGN PATENT DOCUMENTS

| SU | 1326600 A1 | 7/1987 |
| SU | 1685967 A1 | 10/1991 |

OTHER PUBLICATIONS

International Search Report for PCT/BR2015/000085, dated Dec. 10, 2015.

* cited by examiner

*Primary Examiner* — Terressa Boykin
(74) *Attorney, Agent, or Firm* — Sughrue Mion, PLLC

(57) ABSTRACT

The present invention relates to a method for removing organic deposits from oil and gas wells and other subsystem systems comprising cumene and biodiesel. The invention also relates to a method for removing organic deposits, including the steps for pumping said remover composition through a riser and/or through peripheral pipes of the umbilical and/or production pipe, leaving the composition in contact with the deposit for a sufficient time for removal of at least 50% of such.

12 Claims, No Drawings

COMPOSITION FOR REMOVING ORGANIC DEPOSITS FROM OIL AND GAS WELLS AND OTHER SUBSURFACE SYSTEMS AND METHOD FOR REMOVING ORGANIC DEPOSITS USING THE REMOVER COMPOSITION

CROSS REFERENCE TO RELATED APPLICATIONS

This Application is a National Stage of International Application No. PCT/BR2015/000085 filed Jun. 12, 2015, the contents of which are incorporated herein by reference in their entirety.

FIELD OF THE INVENTION

The present invention relates to a composition for removing organic deposits from oil and gas wells and other subsurface systems. More particularly, the present invention relates to a remover composition comprising mixtures of isopropylbenzene and methyl esters of unsaturated vegetable oils (biodiesel). The invention also relates to a method for removing organic deposits using such remover composition.

BACKGROUND OF THE INVENTION

Oil production occurs primarily in offshore fields, from post-salt and pre-salt reservoir rocks, the common characteristic of which is that they are located at great depths below the seabed. This seabed, in turn, is found under water columns that can exceed 3,000 meters in length.

From the reservoir rock to the wellhead, the fluids produced (water, oil, and gas) and the carried sediment travel hundreds or thousands of meters in horizontal, oblique and vertical directions until reaching the Christmas Trees. These fluids and sediments ascend through flexible pipes and rigid pipes called risers from the Christmas Trees to the Stationary Production Units (SPUs).

Environmental conditions outside the subsea well generally involve high pressure and high temperature due to the geothermal gradient that causes a temperature rise of about +1° C. for every 40 meters depth. At the bottom of the sea, in deep waters in Brazil, water temperature is slightly above 0° C.

There is a frequent problem with organic deposits inside various lifting pipe segments, especially in the riser. These deposits are fundamentally complex mixtures of solidified paraffin, resins, asphaltenes and sediments, in addition to all other fluids existing in the well, conditions that may be occluded in the porosities of the deposits. The result of this deposition is the reduction of the useful internal diameter of the pipes and the consequent reduction of the yield of wells and/or Christmas Trees due to flow restrictions and an increase in the loss of load to the surface.

The occurrence of such organic deposits and fouling is a serious problem in well productivity and is usually prevented by adding high cost chemicals such as vinyl acetate copolymers, fatty alcohol polyacrylate and polyphenols to the oil produced, or mechanically prevented, through the preventive use of PIGs. However, in addition to the very high costs, the availability of these products on platforms and the possibility of continuously injecting them represent a great logistical problem at long maritime distances, as well as requiring complex injection operations through peripheral and umbilical pipes, which are not always available.

When it is not possible to prevent organic deposition, a flow restoration is performed. Normally flow restoration is accomplished by injecting a fluid to dissolve the deposit from the SPU, or even by means of mechanical intervention. This restoring fluid, the main function of which is to be a paraffin phase solvent and an asphaltene phase suspender/stabilizer, is injected at high pressure from the SPU to at least the level of the Christmas Tree. It is not uncommon to fill the entire length of the riser and also the production pipe to the deepest section of the well.

The cleaning fluid acts in situ for a period of time, cleaning the inside of the pipes and descaling ancillary equipment such as instruments and valves. After the time of action, the fluid returns to the surface, where it will appropriately come together with most of the deposits responsible for loss of productivity. However, after being used one or more times, said fluid loses its solvent and restorative potential for surfaces, so it is discarded, being disposed of by incorporation into the oil produced.

Among the fluids most used for this cleaning are ketones, kerosene, toluene, xylene, among others. After use, the quantities of this fluid incorporated into the oil are insignificant and will be diluted to infinity at the oil refineries.

Since the interior of the lifting systems includes a volume normally less than 100 $m^3$, the quantity and costs of the fluid represent only a fraction of the benefit of higher productivity of the well, which under optimized conditions yields hundreds or thousands of cubic meters of oil per day. Thus, the criteria of performance, safety, health and availability should be evaluated when choosing the remover fluid.

In terms of performance, light aromatics would be the best choice. However, benzene molecules are known to be carcinogenic and flammable when cold.

Methylbenzene, also known as toluene, is excellent on organic deposits, but this compound has a marked narcotic effect and is also too volatile and flammable when cold.

By increasing the number of carbons of such alkyl benzene to n=8, there are products known as AB-8, in reference to xylene isomers and ethylbenzene. The performance of these products is excellent and their health risks are lower than those of benzene. However, they are volatile and have the appearance of gasoline, as well as being absolutely flammable under deck conditions.

Kerosene, in turn, is a safe product as regards its cold flammability. Its' flash point is established by the ASTM D-56 method at 46° C. It is safer for the users' health and for the environment when compared to aromatics. However, kerosene is generally ineffective in cleaning problematic fouling. On the positive side, it has almost unlimited availability, low cost and is easy.

When working with mixtures, drum logistics must be performed on the deck of the platform as well as risky operations of mixing hazardous fluids aiming to tailor performance to negative externalities such as carcinogenicity, flammability, narcotic effect and cost of component products.

When analyzing the performance of aromatics with a higher number of carbons, such as AB-10 and AB-11, they are not able to adequately dissolve the deposits and fouling. Meanwhile 9-carbon alkyl benzene, sold as mixtures and known under the trade name AB-9, corresponding to the international nomenclature of the Chemical Abstracts Service CAS No. 25551-13-7 and CAS 64742-95-6, offer an excellent compromise between performance, lower cold flammability, risks to health and the environment. These products are certainly suitable and will continue to be used abroad, and also in Brazil, whenever available.

In Brazil, the product that combines the best set of qualities for the proposed removal of deposits, that is, the AB-9—mixture of alkyl benzene with 9 carbons—is very scarce, as it is currently only produced at three petrochemical plants and at one oil refinery. Because it is a product regulated by the National Agency of Oil, Natural Gas and Renewable Fuels (ANP), recipients include fifty authorized consumers who bid for it and who depend on this product for strong economic performance. In this way, Brazilian offshore oil producers do not have access to necessary quantities of AB-9.

Thus, the presented problem reveals the need to find new aromatic based products, with unrestricted availability, deregulated use by the competent authorities, and performance similar to or superior to AB-9.

Numerous attempts at solving the problem of the nature of organic tank-removing fluids in oil production can be found in the prior art. U.S. Pat. No. 4,925,497 reveals a method for removing paraffin and paraffin-like deposits from oil field equipment which involves washing said equipment with a solvent mixture comprising an aromatic hydrocarbon selected from the group consisting of toluene, xylene, mesitylene and mixtures thereof and oil naphtha, the weight ratio of said aromatic hydrocarbon to naphtha being about 10/90 to about 90/10.

Patent SU1326600A1, in turn, proposes the use of a composition for removing deposits of asphalt, resin and wax comprised of 5 to 50% by weight of anisole, 0.1 to 1.0% by weight of polyethylene glycol monoalkyl esters and 49.0 to 94.9% by weight of alkyl aromatic hydrocarbon mixtures consisting of polyalkylbenzene from the production of ethylbenzene or polypropylbenzene from the production of isopropylbenzene.

Patent SU1685967A1 proposes the use of a composition for the removal of asphaltene, resin and paraffin deposits containing 40 to 75% by weight of condensed hydrocarbon and the remainder, a fraction of polyalkyl benzene obtained as a byproduct of the production of isopropylbenzene.

U.S. Pat. No. 4,090,562A describes a method and a composition for stimulating the production of oil in a producing well by the removal of organic deposits. The solvent composition contains 45 to 85% by volume of an aliphatic hydrocarbon, 5 to 45% by volume of benzene, toluene, ethylbenzene, cumene, mesitylene or propylbenzene, 0.56% by volume of ethylene glycol monobutyl ester or monomethyl ester of diethylene glycol and 1 to 15% by volume of methanol, propane, isopropanol or butanol.

Therefore, as shown above, the prior art uses complex mixtures containing aromatic hydrocarbons for removal of organic deposits and fouling.

None of the prior art documents describe a simple, easily obtainable composition to remove organic deposits and fouling, with a simple to obtain high performance aromatic base resulting in faster, economical and safer removal.

As will be better described below, the present invention seeks to resolve the above-described problems of the prior art in a practical and efficient manner.

SUMMARY OF THE INVENTION

The present invention provides for a remover composition, comprising an aromatic ingredient (A) consisting of pure cumene (isopropylbenzene with purity above 99.9%) or contaminated with up to 10% by weight of diisopropylbenzene (DIPB) and up to 3% by weight of triisopropylbenzene (TIPB) based on the weight of cumene and a biodiesel ingredient (B) consisting of methyl esters of vegetable oils rich in polyunsaturated fatty acids.

The present invention also provides for a method for removing organic deposits and fouling that utilizes said composition for removal.

DETAILED DESCRIPTION OF THE INVENTION

The present invention provides an innovative remover composition, presented as a single product, useful in removing organic deposits and fouling commonly found in oil and gas wells.

The remover composition of the present invention is comprised of (A) 75 to 97.5% by weight of pure cumene (isopropylbenzene with purity above 99.9%) or contaminated cumene with up to 10% by weight of diisopropylbenzene and up to 3% by weight of 1,3,5-triisopropylbenzene, based on the total weight of cumene and (B) 2.5 to 25% by weight of biodiesel, consisting of methyl esters derived from vegetable oils rich in polyunsaturated oils.

Biodiesel is produced by transesterification of vegetable oils resulting in glycerol and methyl esters of fatty acids.

When it leaves the plants, pure biodiesel is normally stabilized with antioxidant additives, such as 2,6-di-tert-butyl-4-methyl-phenol (BHT), 2,5-di-tert-butyl hydroquinone (TBHQ), 3-tert-butyl-4-hydroxyanisole (BHA), with concentrations ranging from 100 to 1000 ppm, so that long chains of polyunsaturated fatty acid esters do not react with oxygen forming oxygenated compounds.

Pure cumene has a melting point of −96° C., a boiling point of 152° C., a flash point of 43° C. and viscosity of 0.777 cP at 21° C. Therefore, one of the purposes of biodiesel in the remover composition is to increase the flash point of the composition to above 46° C., since prior to its degradation, biodiesel has a flash point above 115° C. and even after its degradation, its flash point is not less than 100° C., substantially higher than the flash point of pure cumene.

Polyunsaturated oil biodiesel has double bonds in specific positions, so that it oxidizes easily with the oxygen of the air, generating fatty peroxides, for this reason, biodiesel also has the function of an oxygen sequestrant. One of the functions of adding biodiesel to cumene is to act as a sacrificial oxidant to preserve cumene from potential oxidation.

In addition, biodiesel provides polarity and electrical conductivity. Because the paraffins are closely interspersed with polar macromolecules such as resins and asphaltenes molecules, the polarization of the ester group of the biodiesel creates interacting forces with the complexed metals in asphaltenes without impairing the potent solvency of the aromatic ring over the hydrocarbons in general. Moreover, since its price is lower than the price of cumene, it is used as an ingredient to reduce the cost of the solvent.

The biodiesel mixture should initially be restricted to the objective of raising the flash point of the remover mixture (isopropylbenzene-methyl ester) to a point that is considered safe and desirable. Depending on the flash point of the methyl ester, which varies depending on the type of vegetable oil used, the mixing ratio with vegetable methyl ester varies. Compositions containing above 25% by weight of biodiesel and less than 75% by weight of cumene have generally been found to have poor removal action.

Examples of raw materials for biodiesel formulations are the methyl esters of soybean, cotton and sunflower oil.

The cold fluidity properties of the ester vary greatly according to the nature of the vegetable oil, so that more unsaturated fatty esters are advantageously employed. Thus, soybean oil ester is a preferable ester, meaning that commercial methyl isocyanate is a stream suitable for the proposed composition. The flash point of already degraded methyl soya remains above 100° C., which makes it useful to provide cumene with lower cold flammability.

The above-described components, in the above-defined ratios, form a stable organic solution of oily appearance and a light brown color, with pungent odor and a flash point above 46° C.

The present invention also provides for a method for the removal of organic deposits and fouling in oil production. In this sense, the remover composition of the present invention is taken to the oil platforms and pumped through riser and/or through peripheral umbilical pipes, and can be introduced into the internal structures of the wells and formation structures, through the production pipe.

The composition is pumped through the interior of production riser until it fills the entire area of interest, which can range from the lower region of the production column adjacent to the producing rock zone, through the wet Christmas tree to the point of connection between the rigid or flexible production pipe that composes the riser and the SPU.

The time required for contact by the composition depends on the characteristics of the deposits, a time of about 24 hours being generally used, when more than 50% of the deposits have been made soluble and taken to the surface through the production of the remover composition column. Following expulsion of the fluids together with the solubilized deposits, well production is uninterrupted and the remover composition can be reused or mixed with the crude oil produced and then transferred to the oil refinery where it will be redistilled along with the vacuum gasoil streams, undergoing infinite dilution, without impairing refining and processing activities.

Examples are given below corresponding to the scope of the present invention, as well as comparative examples illustrating the state of the art. Note that the following description will be based on preferred embodiments of the invention. As will be apparent to a person skilled in the art, however, the invention is not limited to these particular embodiments.

Example—Test for Dissolution of Organic Deposits

The remover compositions of the invention were tested in a laboratory in accordance with the methodology specified below.

Homogenization of the Organic Deposit

Firstly, the organic deposit was homogenized, consisting of the steps of: i) adding oil to the organic deposit in question, if it is not at the proper consistency for extrusion; and (ii) homogenizing the organic deposit either manually or by a TURRAX mixer, until it is ready for extrusion.

Preparation of the Sample

The extruder cylinder was filled until it was observed that a sample thread came out, indicating that the cylinder was perfectly compacted. The perforated cap was replaced by the nozzle of the extruder and the specimens with a template size fixed in the nozzle of the extruder were created. After that, each specimen was cut with the aid of an electric device and the specimens were placed in a petri dish.

Test

The specimens were weighed, transferred into Schott flasks and 50 ml of the solvent was added. The flasks were then placed in a shake bath at a temperature of 15° C., shaken at about 20 rpm for the time required for the test (6 h, 24 h and 64 h). The mixture was then filtered through a Millipore assembly with a pre-weighed screen and the residue washed with a brief methyl isobutyl ketone (MIBK) spray cooled to −15° C. The residue screen was transferred to a stainless steel tray and inserted in a vacuum oven for 24 hours at 50° C. The material was removed from the oven and allowed to cool to room temperature, in order to weigh the residue. The result was expressed as a dissolution percentage.

The removal performance of organic deposits from the remover composition comprising 95% cumene (purity over 99%)+5% commercial biodiesel of the present invention, was evaluated and compared to the performance of other remover solvents, namely xylene, diesel and AB-9. Average reduction of organic deposits and performance (compared to AB-9) results are listed in Table 1 below.

TABLE 1

Comparative results of the reduction of organic deposits

| Type of oil | Remover product | Average reduction of organic deposits (%) | Performance compared to AB-9 (Δ %) |
|---|---|---|---|
| Heavy aromatic naphthenic | Remover composition of the invention (95% cumene + 5% biodiesel) | 33.9 | −11.6 |
| | Xylene | 42.0 | −3.4 |
| | Diesel | 21.8 | −67.3 |
| | AB-9 | 45.5 | N/A |
| Medium paraffin | Remover composition of the invention (95% cumene + 5% biodiesel) | 98.6 | −0.9 |
| | Diesel | 6.1 | −93.4 |
| | AB-9 | 99.5 | N/A |

Based on the results under Table 1 above, note that the composition of the present invention has satisfactory performance in the removal of organic deposits when compared to more dangerous and scarce AB-9s solvents.

Other advantages of the remover composition are the unlimited and unregulated supply of the components of such, its ability to improve the productivity of oil and gas production systems and use in small quantities. In addition, the remover composition has a low health risk and, due to its higher flash point, is safer as regards its cold flammability, and has satisfactory performance in removing organic deposits and fouling.

Numerous variations to the scope of protection of the present patent application are permitted. Thus, it is emphasized that the present invention is not limited to the particular configurations/embodiments described above.

The invention claimed is:

1. A remover composition of organic deposits and fouling in oil and gas wells and other subsurface systems, comprising (A) 75% to 97.5% by weight of cumene and (B) 2.5 to 25% by weight of biodiesel.

2. The remover composition according to claim 1, wherein the composition comprises 95% by weight of cumene and 5% by weight of biodiesel.

3. The remover composition according to claim 1, wherein the cumene consists of pure cumene (isopropylbenzene with purity above 99.9%) or contaminated cumene with up to 10% by weight of diisopropylbenzene (DIPB) and up to 3% by weight of 1,3,5-triisopropylbenzene (TIPB), based on cumene weight.

4. The remover composition according to claim 1, wherein the biodiesel comprises methyl esters derived from polyunsaturated-rich vegetable oils selected from the group consisting of soybean, cotton and sunflower oil.

5. The remover composition according to claim 4, wherein the biodiesel comprises antioxidant additives selected from the group consisting of 2,6-di-tert-butyl-4-methyl-phenol (BHT), 2,5-di-tert-butyl hydroquinone (TBHQ) and 3-tert-butyl-4-hydroxyanisole (BHA).

6. The remover composition of claim 5, wherein the concentration of the oxidizing additive ranges from 100 to 1000 ppm.

7. The remover composition of claim 4, wherein the methyl ester is methyl isoate.

8. The remover composition according to claim 1, which has a flash point above 46° C.

9. A method for removing organic deposits, comprising the steps of:
    pumping the remover composition as defined in claim 1 through a riser and/or through peripheral pipes of umbilical and/or production pipes;
    leaving the composition in contact with the deposit for a time sufficient to remove at least 50% of such;
    removing the dissolved and conducted organic deposits and conducting them to the surface with the remover composition.

10. The method according to claim 9, wherein, after use, the remover composition is separated to be used in another well.

11. The method according to claim 9, wherein, after use, the remover composition is mixed with the crude oil produced and then transferred to an oil refinery where it is redistilled together with vacuum gasoil streams, undergoing infinite dilution.

12. The remover composition according to claim 4, wherein the biodiesel comprises methyl esters derived from soybean oil.

* * * * *